United States Patent
Willey et al.

(10) Patent No.: US 8,563,238 B2
(45) Date of Patent: Oct. 22, 2013

(54) METHOD FOR QUANTITATIVE MEASUREMENT OF GENE EXPRESSION FOR IDENTIFYING INDIVIDUALS AT RISK FOR BRONCHOGENIC CARCINOMA

(75) Inventors: James C. Willey, Toledo, OH (US); David A. Weaver, Perrysburg, OH (US); Erin L. Crawford, Rossford, OH (US)

(73) Assignee: University of Toledo, Toledo, OH (US)

( * ) Notice: Subject to any disclaimer, the term of this patent is extended or adjusted under 35 U.S.C. 154(b) by 390 days.

(21) Appl. No.: 11/757,705

(22) Filed: Jun. 4, 2007

(65) Prior Publication Data

US 2008/0311569 A1 Dec. 18, 2008
US 2012/0322071 A9 Dec. 20, 2012

Related U.S. Application Data

(63) Continuation of application No. 10/471,473, filed as application No. PCT/US02/07259 on Mar. 12, 2002, now abandoned.

(60) Provisional application No. 60/275,854, filed on Mar. 14, 2001.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| | | |
|---|---|---|
| 5,639,606 A | 6/1997 | Willey |
| 5,643,765 A | 7/1997 | Willey |
| 5,876,978 A | 3/1999 | Willey et al. |
| 2003/0186246 A1 | 10/2003 | Willey et al. |

FOREIGN PATENT DOCUMENTS

WO  WO 02/072866 A2  9/2002

OTHER PUBLICATIONS

Alms, et al. Simultaneous quantitation of cytokine mRNAs by reverse transcription-polymerase chain reaction using multiple internal standard cRNAs. Diagn Mol Pathol. Jun. 1996;5(2):88-97.
Crawford, et al. Normal bronchial epithelial cell expression of glutathione transferase P1, glutathione transferase M3, and glutathione peroxidase is low in subjects with bronchogenic carcinoma. Cancer Res. 2000; 60, 1609-18.
Nakayama, et al. Quantification of mRNA by non-radioactive RT-PCR and CCD imaging system. Nucleic Acids Res. Sep. 25, 1992;20(18):4939.
Raeymaekers, L. Quantitative PCR: theoretical considerations with practical implications. Anal Biochem. Nov. 1, 1993;214(2):582-5.
Reischl, et al. Quantitative PCR. A survey of the present technology. Mol Biotechnol. Feb. 1995;3(1):55-71.
Vanden Heuvel, et al. Dioxin-responsive genes: examination of dose-response relationships using quantitative reverse transcriptase-polymerase chain reaction. Cancer Res. Jan. 1, 1994;54(1):62-8.
Wang, et al. Quantitation of mRNA by the polymerase chain reaction. Proc Natl Acad Sci U S A. Dec. 1989;86(24):9717-21.
Willey, et al. Decreased expression levels of glutathione transferase P1, CC10 and thermolabile phenol sulfortransferase genes in normal bronchial epithelial cells from lung cancer patients. #1636, Proceedings of American Association for Cancer Research Annual Meeting. Mar. 1999; 40:247.
Willey, et al. Expression measurement of many genes simultaneously by quantitative RT-PCR using standardized mixtures of competitive templates. Am. J. Resp. Cell Mol. Biol. 1998. 19:6-17.
Zamorano, et al. Quantitative RT-PCR for neuroendocrine studies. Neuroendocrinology. 1996; 63(5):397-407.
Zimmermann, et al. Technical aspects of quantitative competitive PCR. Biotechniques. Aug. 1996;21(2):268-72, 274-9.

*Primary Examiner* — Teresa E Strzelecka

(74) *Attorney, Agent, or Firm* — MacMillan, Sobanski & Todd, LLC

(57) ABSTRACT

A method measure expression of multiple target genes in a progenitor cell for bronchogenic carcinoma comprising the use of reverse transcription-polymerase chain reaction (RT-PCR) to allow simultaneous expression measurement of the multiple target genes is disclosed.

8 Claims, 8 Drawing Sheets

Figure 1
(Table 1 Demographic Data)

| Subject | Diagnosis | Gender | Age | Ethnic Status | Sm Hx[a] | Pack Year[b] |
|---|---|---|---|---|---|---|
| 1 | normal | M | 24 | white | - | 0 |
| 4 | normal | M | 27 | other[c] | - | 0 |
| 5 | normal | M | 28 | white | - | 0 |
| 7 | normal | M | 25 | white | - | 0 |
| 8 | normal | F | 26 | white | - | 0 |
| 9 | normal | F | 26 | other | - | 0[d] |
| 10 | normal | M | 27 | white | - | 0 |
| 11 | normal | F | 21 | white | + | 4 |
| 12 | normal | M | 23 | other | + | 8 |
| 13 | normal | F | 32 | white | + | 9 |
| 16 | normal | F | 39 | white | + | 20 |
| 20 | normal | F | 24 | white | - | 0 |
| 21 | normal | F | 23 | other | - | 0 |
| 54 | organ donor/COPD[e] | F | 55 | white | + | 30 |
| 55 | organ donor/asthma | M | 50 | white | - | 0 |
| 57 | colonic adenocarcinoma | M | 60 | white | - | 0 |
| 59 | COPD | F | 50 | white | - | 0 |
| 62 | organ donor/COPD | F | 58 | white | + | 37 |
| 63 | COPD | M | 70 | white | + | 75 |
| 64 | COPD | F | 47 | white | + | 45 |
| 65 | granuloma | F | 51 | white | - | 0 |
| 66 | COPD | F | 54 | white | + | 30 |
| 71 | colonic adenocarcinoma | M | 60 | white | - | 0 |
| B1 | NSCLC[f] | F | 77 | white | former[g] | 40 |
| B2 | adenocarcinoma | F | 46 | white | former | 40 |
| B3 | squamous cell carcinoma | M | 63 | white | former | 60 |
| 31 | adenocarcinoma | M | 90 | white | former | 100 |
| 32 | adenocarcinoma | F | 75 | other | former | 25 |
| 33 | NSCLC | F | 62 | white | former | 30 |
| 34 | NSCLC | M | 80 | white | former | 40 |
| 53 | NSCLC | F | 49 | other | former | 45 |
| 60 | squamous cell carcinoma | M | 73 | white | + | 125 |
| 74 | NSCLC | M | 70 | white | former | na[h] |
| 75 | squamous cell carcinoma | M | 72 | white | former | 50 |
| 10525 | normal cultured | F | 49 | white | former | 125 |
| 17378 | normal cultured | M | 10 | white | - | 0 |
| 17684 | normal cultured | M | 20 | white | + | 8 |
| 17714 | normal cultured | F | 60 | white | + | na |
| 6F0333 | normal cultured | F | 41 | white | - | 0 |
| 6F0395 | normal cultured | M | 22 | white | + | 2 |
| 6F0450 | normal cultured | F | 16 | other | - | 0 |
| 7F0075 | normal cultured | F | 29 | white | na | na |

[a] Sm Hx refers to smoking history. + = smoker, - = non-smoker, former = former smoker; [b] Pack years were calculated by multiplying the number of packs smoked per day by the number of years smoked at each rate; [c] Subjects 4 and 9 are from the Asian subcontinent, Subjects 21 and 6F0450 are Hispanic, Subject 12 is Asian, and Subjects 18, 53 and 32 are black; [d] Subjects 9 and 10 smoked an occasional cigarette, none within a week prior to bronchoscopy; [e] COPD = chronic obstructive pulmonary disease; [f] NSCLC = non-small cell lung cancer; [g] Subject B1 quit smoking one month prior to bronchoscopy. All other former smokers quit at least 2 years prior to bronchoscopy; [h] na= data not available.

Figure 2 (Table 1 - Primer sequences and positions)

| Gene | Primer | Sequence | Position | Product |
|------|--------|----------|----------|---------|
| β-Actin | Forward | 5' GAT TCC TAT GTG GGC GAC GAG 3' | 192-212 | |
| | Reverse | 5' CCA TCT CTT GCT CGA AGT CC 3' | 704-723 | 532 bp |
| | CT | 5' CCA TCT CTT GCT CGA AGT CCG CCA GCC AGG TCC AGA CGC A 3' | 568-587 | 416 bp |
| GSHPx | Forward | 5' CCT GGT GCT GGT GCT CGG CTT CC 3' | 522-541 | |
| | Reverse | 5' CAA TGG TCT GGA AGC GGC GG 3' | 852-871 | 350 bp |
| | CT | 5' CAA TGG TCT GGA AGC GGC GGA CCG GAG ACC AGG TGA TGA G 3' | 757-776 | 279 bp |
| GSHPxA | Forward | 5' GCA GAG CCG GGG ACA AGA GAA 3' | 113-133 | |
| | Reverse | 5' CTG CTC TTT CTC TCC ATT GAC 3' | 471-491 | 379 bp |
| | CT | 5' CTG CTC TTT CTC TCC ATT GAC GCT CTT CCT GTA GTG CAT TCA 3' | 298-318 | 227 bp |
| GSTM1,2,4, | Forward | 5' GGG ACG CTC CTG ATT ATG AC 3' | 122-141 | |
| | Reverse | 5' GCA AAC CAT GGC CGC TTC CC 3' | 442-461 | 340 bp |
| | CT | 5' GCA AAC CAT GGC CGC TTC CCT TCT CCA AAA TGT CCA CAC G 3' | 301-320 | 219 bp |
| GSTM3 | Forward | 5' GTG CGA GTC GTC TAT GGT TC 3' | 23-52 | |
| | Reverse | 5' AGT TGT GTG CGG AAA TCC AT 3' | 342-361 | 339 bp |
| | CT | 5' AGT TGT GTG CGG AAA TCC ATT GCT CTG GGT GAT CTT GTT C 3' | 230-249 | 247 bp |
| GSTP1 | Forward | 5' TCC GCT GCA AAT ACA TCT CC 3' | 305-324 | |
| | Reverse | 5' TGT TTC CCG TTG CCA TTG AT 3' | 616-635 | 331 bp |
| | CT | 5' TGT TTC CCG TTG CCA TTG ATT AGG ACC TCA TGG ATC AGC A 3' | 485-504 | 220 bp |
| GSTT1 | Forward | 5' GCT CTA CCT GGA CCT GCT GT 3' | 12-31 | |
| | Reverse | 5' GGA ACA CAG GGA ACA TCA CC 3' | 351-370 | 359 bp |
| | CT | 5' GGA ACA CAG GGA ACA TCA CCT AGA GCA GGA TGG CCA CAC T 3' | 199-218 | 227 bp |
| mGST | Forward | 5' CAA AAT TGA AAA AAT GGT TGA CCT CA 3' | 61-86 | |
| | Reverse | 5' TCT ATT TGG CTG GGG AAG GGG TGT CA 3' | 438-463 | 403 bp |
| | CT | 5' TCT ATT TGG CTG GGG AAG GGG TGT CAG GGG TCG GGA CCA CTC AAG GAA TAC A 3' | 348-373 | 339 bp |

Figure 3

(Table 3 - Glutathione Transferase and Peroxidase Gene Expression
(mRNA/10³ β-Actin mRNA) in Primary Bronchial Epithelial Cells from Subjects without Bronchogenic Carcinoma)

| SUBJECT | | GSTM1,2,4,5 | GSTM3 | GSTP1 | GSTT1 | mGST | GSHPx | GSHPxA | Index[b] |
|---|---|---|---|---|---|---|---|---|---|
| 1 | MEAN | 3.62 | 0.31 | 278 | 1.88 | 1.98 | 70.0 | 1.02 | $3.85 \times 10^{-2}$ |
| | S or R[a] | 2.14 S | 0.22 S | 150 S | 1.61 S | 1.02 R | 6.62 S | 0.74 S | |
| 4 | MEAN | 1.00 | 0.06 | 103 | 0.41 | 23.5 | 55.8 | 0.15 | $1.35 \times 10^{-1}$ |
| | S or R | 0.32 S | 0.05 S | 37.8 S | 0.29 S | 5.99 S | 26.5 S | 0.15 S | |
| 5 | MEAN | 0.55 | 0.01 | 86.1 | 0.33 | 22.7 | 160 | 0 | $3.52 \times 10^{-1}$ |
| | S or R | 0.47 R | <0.01 R | 65.8 S | 0.10 S | 12.6 S | 34.6 S | 0.02 R | |
| 7 | MEAN | 0.54 | 0.04 | 80.4 | 0.64 | 19.1 | 62.4 | 0.21 | $9.58 \times 10^{-2}$ |
| | S or R | 0.36 S | <0.01 S | - | 0.26 S | 3.35 S | 10.2 S | 0.05 S | |
| 8 | MEAN | 0.35 | 0.01 | 335 | 0.27 | 6.24 | 167 | 0.08 | $3.49 \times 10^{-1}$ |
| | S or R | 0.16 R | <0.01 S | 289 S | 0.12 S | 1.88 S | 115 S | 0.01 S | |
| 9 | MEAN | 0.78 | 0.31 | 388 | 1.00 | 2.22 | 301 | 0.28 | $2.59 \times 10^{-1}$ |
| | S or R | 0.44 S | 0.44 R | 53.2 S | - | 0.93 S | 146 S | 0.28 R | |
| 10 | MEAN | 1.16 | 0.11 | 249 | 2.75 | 5.19 | 143 | 0.92 | $1.85 \times 10^{-1}$ |
| | S or R | 0.59 R | 0.07 R | 172 S | 0.46 S | 0.74 R | 48.5 S | 0.80 S | |
| 11 | MEAN | 0.50 | na[c] | 111 | 0.06 | 18.0 | 94.0 | 0.50 | $1.88 \times 10^{-1}$ |
| | S or R | 0.29 R | | 37.9 S | - | 16.2 R | 18.8 S | 0.86 R | |
| 12 | MEAN | 0.32 | 0.24 | 581 | 1.77 | 20.5 | 346 | 0.54 | $4.12 \times 10^{0}$ |
| | S or R | 0.35 R | 0.11 S | 447 S | 0.57 S | 5.28 S | 214 S | 0.01 S | |
| 13 | MEAN | 1.84 | 0.40 | 299 | 0.55 | 21.1 | 125 | 0.66 | $7.89 \times 10^{-1}$ |
| | S or R | 0.29 R | - | 12.0 R | - | 16.9 S | - | - | |
| 16 | MEAN | 0.55 | na | 62.6 | 0.68 | 1.97 | 114 | 0.22 | $1.41 \times 10^{-2}$ |
| | S or R | 0.36 R | - | 20.1 R | 0.52 R | 1.00 S | 46.6 R | 0.00 R | |
| 20 | MEAN | 0.57 | 0.07 | 215 | nd[d] | 32.2 | 98.5 | 0.33 | $6.82 \times 10^{0}$ |
| | S or R | 0.21 S | 0.04 S | 178 S | - | 3.88 S | 73.7 S | 0.27 S | |
| 21 | MEAN | 0.57 | 0.28 | 635 | 2.11 | 31,800 | 331 | 0.87 | $6.68 \times 10^{3}$ |
| | S or R | 0.11 S | 0.10 S | 108 R | 0.56 S | 28,300 S | 1.00 R | 0.42 S | |
| 54 | MEAN | 2.64 | 1.62 | 394 | nd | 272 | 173 | 0.33 | $1.85 \times 10^{1}$ |
| | S or R | 4.26 R | 2.31 R | 395 S | - | 280 S | 36.1 S | 0.09 R | |
| 55 | MEAN | 1.31 | 0.61 | 510 | 0.36 | 10.3 | 149 | nd | $7.83 \times 10^{-1}$ |
| | S or R | 0.45 S | 0.13 S | 156 S | 0.18 S | 2.00 S | 10.1 S | - | |
| 57 | MEAN | 0.57 | 0.19 | 604 | 1.68 | 12.0 | 265 | 0.67 | $1.92 \times 10^{0}$ |
| | S or R | 0.17 S | 0.08 S | 318 S | 0.49 S | 1.40 S | 42.9 S | 0.33 S | |
| 59 | MEAN | 0.45 | 0.06 | 370 | 0.49 | 14.0 | 110 | 0.43 | $5.70 \times 10^{-1}$ |
| | S or R | 0.22 S | 0.04 S | 166 S | 0.15 S | 1.10 S | 20.0 S | 0.27 S | |
| 62 | MEAN | 0.39 | 0.15 | 220 | 0.12 | 22.7 | 95.8 | 0.25 | $4.78 \times 10^{-2}$ |
| | S or R | 0.07 S | 0.11 S | 141 S | 0.02 S | 6.26 S | 6.51 S | 0.17 S | |
| 63 | MEAN | 0.30 | 0.17 | 80.6 | 0.22 | 8.12 | 32.2 | nd | $2.11 \times 10^{-2}$ |
| | S or R | 0.11 S | 0.06 S | 33.3 S | 0.02 S | 2.52 S | 17.6 S | - | |
| 64 | MEAN | 0.84 | 0.29 | 64.8 | 0.24 | 9.98 | 35.9 | nd | $2.32 \times 10^{-2}$ |
| | S or R | 0.72 R | 0.28 S | 18.3 S | 0.03 S | 4.38 S | 9.39 S | - | |
| 65 | MEAN | 1.46 | 0.61 | 195 | 0.70 | 17.5 | 36.0 | nd | $1.23 \times 10^{-1}$ |
| | S or R | 0.22 R | <0.01 R | 3.79 S | 0.14 S | 1.43 S | 15.3 S | - | |
| 66 | MEAN | 1.31 | 0.30 | 208 | 0.53 | 14.6 | 56.7 | 0.21 | $1.72 \times 10^{-1}$ |
| | S or R | 0.49 S | 0.04 S | 15.6 S | 0.23 S | 4.68 S | 21.2 S | <0.0 R | |
| 71 | MEAN | 0.84 | 0.23 | 528 | na | 16.3 | 174 | 0.45 | $1.50 \times 10^{0}$ |
| | S or R | 0.12 S | 0.05 S | 177 S | - | - | 5.77 S | - | |
| GROUP MEANS | | 0.98 | 0.29 | 287 | 0.84 | 26.0[e] | 140 | 0.43 | $1.70 \times 10^{0,f}$ |
| FOLD VARIATION (INTER-SUBJECT) | | 11 | 162 | 10 | 46 | 139 | 11 | 25 | |

[a] S=Standard deviation (calculated when three or more determinations were made) R=range of two determinations which was calculated as the difference between the greater and lesser value. [b] Not assessed due to insufficient amounts of cDNA. [c] None detected. [d] Mean for mGST was calculated excluding value for subject 21. See text for explanation.

Figure 4
(Table 4-Glutathione Transferase and Peroxidase Gene Expression (mRNA/$10^3$ β-Actin mRNA) in Primary Bronchial Epithelial Cells from Subjects with Bronchogenic Carcinoma)

| SUBJECT | | GSTM1,2,4,5 | GSTM3 | GSTP1 | GSTT1 | mGST | GSHPx | GSHPxA |
|---|---|---|---|---|---|---|---|---|
| B1 | MEAN | 0.95 | na[b] | 239 | 0.86 | 5.56 | 25.5 | na |
|    | S or R[a] | 0.59 R | - | 163 S | 0.26 R | 2.83 S | - | - |
| B2 | MEAN | 0.78 | 0.04 | 69.6 | 1.86 | 10.4 | 18.9 | 0.34 |
|    | S or R | 0.51 S | <0.01 R | 25.2 S | 1.56 S | 3.27 S | 8.90 R | 0.29 R |
| B3 | MEAN | 0.48 | 0.04 | 39.0 | 1.37 | 5.04 | 31.8 | 0.18 |
|    | S or R | 0.23 S | 0.03 S | 11.7 S | 0.31 S | 1.17 S | 19.9 S | 0.12 R |
| 31 | MEAN | 0.15 | 0.03 | 43.7 | 0.01 | 1.74 | 16.0 | 0.19 |
|    | S or R | 0.05 S | 0.01 S | 26.7 S | <0.01 S | 0.57 S | 15.8 R | 0.08 R |
| 32 | MEAN | 0.39 | 0.16 | 210 | 0.49 | 5.45 | 62.0 | 0.25 |
|    | S or R | 0.31 S | 0.16 R | 55.0 S | 0.38 S | 2.36 S | 61.0 S | 0.20 R |
| 33 | MEAN | 0.71 | 0.04 | 30.1 | 0.41 | 1.54 | 29.3 | 0.16 |
|    | S or R | 0.12 S | 0.01 S | 17.0 S | 0.17 S | 0.36 S | 13.8 S | 0.07 R |
| 34 | MEAN | 0.13 | 0.06 | 110 | nd[c] | 13.3 | 64.4 | 0.26 |
|    | S or R | 0.04 S | 0.02 S | 70.5 S | - | 5.69 S | 13.1 S | 0.31 S |
| 53 | MEAN | 0.98 | 0.16 | 187 | 1.15 | 10.3 | 63.7 | 0.15 |
|    | S or R | 0.37 S | 0.04 S | 5.20 S | 0.31 S | 1.16 S | 7.37 S | 0.06 R |
| 60 | MEAN | 0.25 | 0.07 | 105 | 0.36 | 6.18 | 62.8 | 0.22 |
|    | S or R | 0.08 S | 0.03 S | 59.7 S | 0.12 S | 0.92 S | 10.1 S | 0.04 S |
| 74 | MEAN | 1.34 | 0.15 | 151 | 0.57 | 7.61 | 180 | 0.53 |
|    | S or R | 0.20 S | 0.07 S | 33.5 S | 0.18 S | 3.66 S | 91.5 S | 0.25 S |
| 75 | MEAN | 0.39 | 0.10 | 20.5 | 0.52 | 3.05 | 129 | 1.10 |
|    | S or R | 0.17 | - | - | - | 4.01 R | 21.8 S | - |
| GROUP MEANS | | 0.60 | 0.09[d] | 110 | 0.76 | 6.11 | 62.1 | 0.34 |
| FOLD VARIATION (INTER-SUBJECT) | | 10 | 5 | 12 | 186 | 7 | 11 | 7 |

[a] S=Standard deviation (calculated when three or more determinations were made) R=range of two determinations which was calculated as the difference between the greater and lessor value. [b] Not assessed due to insufficient amounts of cDNA. [c] None detected. [d] Bold font indicates a statistically significant (p < 0.05) difference from non-bronchogenic carcinoma subject means (Table III).

Figure 5

(Table 5-Glutathione Transferase and Peroxidase Gene Expression (mRNA/$10^3$ β-Actin mRNA) in Cultured Bronchial Epithelial Cells from Subjects without Bronchogenic Carcinoma)

| CELL LINE | | GSTM1,2,4,5 | GSTM3 | GSTP1 | GSTT1 | mGST | GSHPx | GSHPxA |
|---|---|---|---|---|---|---|---|---|
| 10525 | MEAN | 0.03 | 0.03 | 18.3 | 0.04 | 2.05 | 169 | 0.32 |
|  | S or R[a] | 0.02 S | 0.02 S | 11.6 S | 0.01 S | 1.84 S | 14.9 S | 0.18 S |
| 17387 | MEAN | 0.08 | 0.04 | 16.7 | 0.05 | 3.88 | 40.9 | 0.38 |
|  | S or R | 0.10 S | 0.04 S | 6.57 S | 0.05 S | 2.48 S | 15.9 S | 0.17 S |
| 17684 | MEAN | 0.03 | 0.06 | 17.1 | nd[b] | 1.83 | 56.2 | 0.27 |
|  | S or R | 0.03 S | 0.02 S | 6.47 S | - | 1.02 S | 26.3 S | 0.02 S |
| 17714 | MEAN | 0.16 | 0.11 | 16.8 | 0.05 | 3.08 | 36.2 | 0.21 |
|  | S or R | 0.12 S | 0.05 S | 11.6 S | 0.01 S | 0.89 S | 12.6 S | 0.07 S |
| 6F0333 | MEAN | 0.11 | 0.08 | 29.9 | 0.01 | 6.24 | 37.2 | 0.43 |
|  | S or R | 0.03 S | 0.03 S | 7.48 S | <0.01 R | 3.64 S | 8.27 S | 0.09 S |
| 6F0395 | MEAN | 0.04 | 0.08 | 16.4 | 0.06 | 5.43 | 53.0 | 0.30 |
|  | S or R | <0.01 S | 0.04 S | 9.85 S | 0.02 S | 0.68 S | 10.3 S | 0.05 S |
| 6F0450 | MEAN | nd | 0.03 | 37.1 | 0.03 | 6.92 | 48.2 | 0.33 |
|  | S or R | - | 0.01 R | 12.6 S | <0.01 R | 2.52 S | 11.6 S | 0.07 S |
| 7F0075 | MEAN | 0.03 | 0.05 | 10.7 | 0.02 | 3.32 | 30.2 | 0.32 |
|  | S or R | 0.03 S | 0.02 S | 0.92 R | <0.01 S | 0.83 S | 9.59 S | 0.10 S |
| ROUP MEANS | | 0.07 | 0.06 | 20.4 | 0.04 | 4.09 | 58.9 | 0.32 |
| OLD VARIATION (INTER-SUBJECT) | | 5 | 4 | 3 | 6 | 4 | 6 | 2 |

[a] S=Standard deviation (calculated when three or more determinations were made) R=range of two determinations which was calculated as the difference between the greater and lessor value. [b] None detected.

Figure 6

(Table 6-Gene Expression Test to Identify Normal Bronchial Epithelial Cells from Subjects with Bronchogenic Carcinoma)

| Gene or Index[a] | Range of Cut-off values tested[b] | Increment | Best Cut-off Value | | Sensitivity | Specificity |
|---|---|---|---|---|---|---|
| GSTT1 | $5 \times 10^{-1}$ - $5.6 \times 10^{-1}$ | $2 \times 10^{-2}$ | $5.4 \times 10^{-1}$ | | 50% | 50% |
| GSTM1,2,4,5 | $4 \times 10^{-1}$ - $5.6 \times 10^{-1}$ | $2 \times 10^{-2}$ | $4.8 \times 10^{-1}$ | | 55% | 78% |
| GSTP1 | $8 \times 10^{1}$ - $1.3 \times 10^{2}$ | $1 \times 10^{1}$ | $1.1 \times 10^{2}$ | | 64% | 74% |
| GSHPxA | $2 \times 10^{-1}$ - $3.4 \times 10^{-1}$ | $2 \times 10^{-2}$ | $2.8 \times 10^{-1}$ - $3.2 \times 10^{-1}$ | | 70% | 56% |
| GSTM3 | $8 \times 10^{-2}$ - $1.2 \times 10^{-1}$ | $2 \times 10^{-2}$ | $1.0 \times 10^{-1}$ | | 70% | 71% |
| mGST | $4 \times 10^{0}$ - $9.0 \times 10^{0}$ | $1 \times 10^{0}$ | $8.0 \times 10^{0}$ | | 73% | 77% |
| GSHPx | $6 \times 10^{1}$ - $1.0 \times 10^{2}$ | $1 \times 10^{1}$ | $7.0 \times 10^{1}$ - $9.0 \times 10^{1}$ | | 82% | 70% |
| GSTM3 x GSTP1 x mGST | $8 \times 10^{-5}$ - $1.1 \times 10^{-4}$ | $1 \times 10^{-5}$ | $9.0 \times 10^{-5}$ - $1.0 \times 10^{-4}$ | | 70% | 86% |
| GSTM3 x GSHPx | $8 \times 10^{-3}$ - $1.2 \times 10^{-2}$ | $2 \times 10^{-3}$ | $1.0 \times 10^{-2}$ | | 80% | 71% |
| mGST x GSTM3 x GSHPx | $4 \times 10^{-5}$ - $8.0 \times 10^{-5}$ | $1 \times 10^{-5}$ | $6.0 \times 10^{-5}$ - $7.0 \times 10^{-5}$ | | 80% | 76% |
| GSTP1 x GSHPx x GSTM3 | $2 \times 10^{-3}$ - $2.7 \times 10^{-3}$ | $1 \times 10^{-4}$ | $2.1 \times 10^{-3}$ - $2.6 \times 10^{-3}$ | | 90% | 71% |
| mGST x GSTM3 x GSHPx x GSHPxA x GSTP1 | $1 \times 10^{-9}$ - $1.1 \times 10^{-8}$ | $1 \times 10^{-9}$ | $3.0 \times 10^{-9}$ - $1.0 \times 10^{-8}$ | | 90% | 76% |
| GSTP1 x mGST x GSHPx | $9 \times 10^{-2}$ - $1.5 \times 10^{-1}$ | $1 \times 10^{-2}$ | $1.3 \times 10^{-1}$ | | 91% | 74% |
| mGST x GSTM3 x GSHPx x GSTP1 | $3 \times 10^{-5}$ - $3.7 \times 10^{-5}$ | $1 \times 10^{-6}$ | $3.2 \times 10^{-5}$ - $3.5 \times 10^{-5}$ | | 100% | 62% |

[a] See text for explanation of index calculations. [b] Cut-off values are reported as molecules/$10^3$ β-actin molecules.

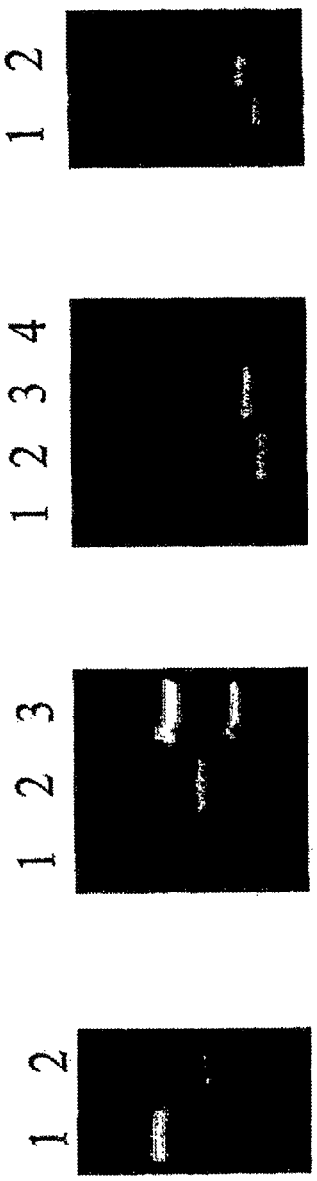
Figures 7a-d

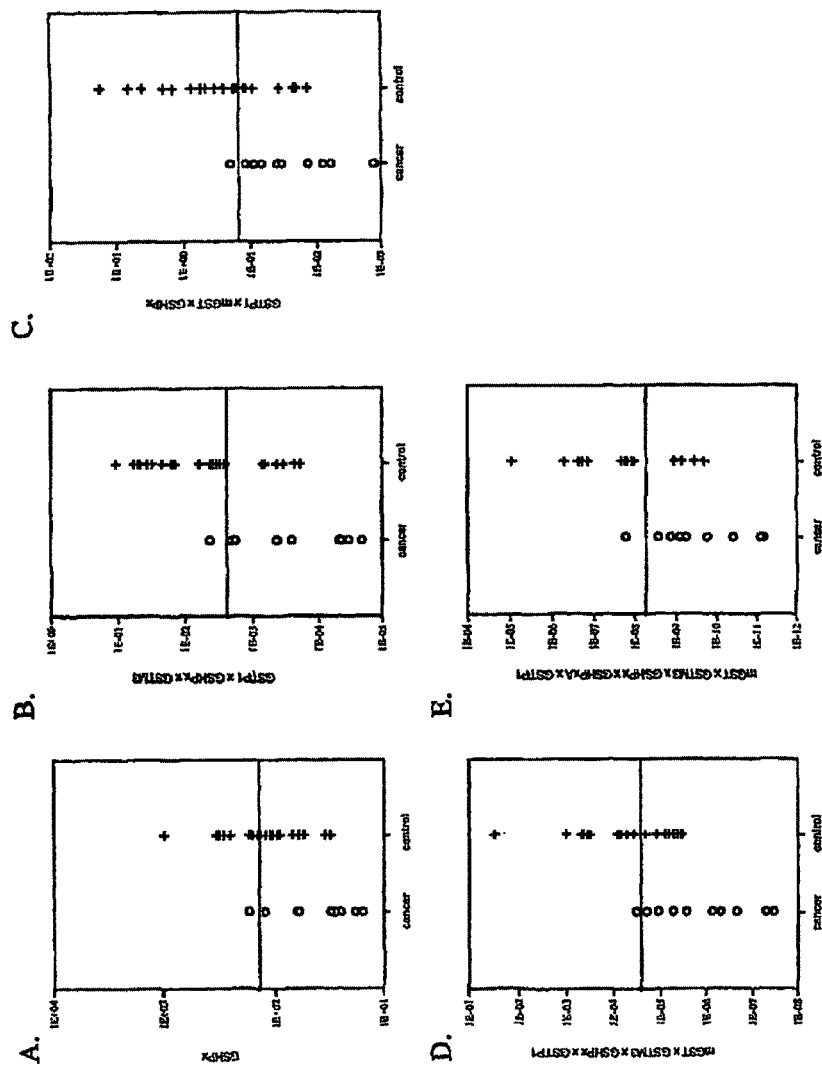

SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gattcctatg tgggcgacga g                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccatctcttg ctcgaagtcc                                                20

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccatctcttg ctcgaagtcc gccagccagg tccagacgca                          40

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctggtggtg ctcggcttcc                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caatggtctg gaagcggcgg                                                20

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 6
caatggtctg aagcggcgg accggagacc aggtgatgag                            40

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcagagccgg ggacaagaga a                                               21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctgctctttc tctccattga c                                               21

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgctctttc tctccattga cgctcttcct gtagtgcatt ca                        42

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggacgctcc tgattatgac                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcaaaccatg gccgcttccc                                                 20

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 12
gcaaaccatg ccgcttccc ttctccaaaa tgtccacacg                              40

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtgcgagtcg tctatggttc                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agttgtgtgc ggaaatccat                                                  20

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agttgtgtgc ggaaatccat tgctctgggt gatcttgttc                            40

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tccgctgcaa atacatctcc                                                  20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgtttcccgt tgccattgat                                                  20

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 18
tgtttcccgt tgccattgat taggacctca tggatcagca                              40

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctctacctg gacctgctgt                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggaacacagg gaacatcacc                                                   20

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggaacacagg gaacatcacc tagagcagga tggccacact                              40

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caaaattgaa aaaatggttg acctca                                            26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tctatttggc tggggaaggg gtgtca                                            26

<210> SEQ ID NO 24
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 24
tctatttggc tggggaaggg gtgtcagggg tcgggaccac tcaaggaata ca          52
```

METHOD FOR QUANTITATIVE MEASUREMENT OF GENE EXPRESSION FOR IDENTIFYING INDIVIDUALS AT RISK FOR BRONCHOGENIC CARCINOMA

CROSS-REFERENCE

This application is a continuation of U.S. application Ser. No. 10/471,473, filed Mar. 11, 2004, now abandoned, which application is incorporated herein by reference—in its entirety, which is a U.S. National Stage Filing of PCT International Application No. PCT/US02/07259, filed Mar.12, 2002, which claims priority to U.S. Provisional application Ser. No. 60/275,854, filed Mar. 14, 2001.

STATEMENT AS TO FEDERALLY SPONSORED RESEARCH

The present invention was made under a Research Grant No. NIH-P01 ES07168 from the National Institute of Health who may have certain rights thereto. The present invention relates generally to a method for the quantitative measurement of gene expression using multiplex competitive reverse transcription polymerase chain reaction (MC RT-PCR). To identify individuals at risk for bronchogenic carcinoma.

BACKGROUND OF THE INVENTION

The PCR techniques are generally described in U.S. Pat. Nos. 4,683,195; 4,683,202 and 4,965,188. The PCR technique generally involves a process for amplifying any desired specific nucleic acid sequence contained within a nucleic acid molecule. The PCR process includes treating separate complementary strains of the nucleic acid with an excess of two oligonucleotide primers. The primers are extended to form complementary primer extension products which act as templates for synthesizing the desired nucleic acid sequence. The PCR process is carried out in a simultaneous step-wise fashion and can be repeated as often as desired in order to achieve increased levels of amplification of the desired nucleic acid sequence. According to the PCR process, the sequence of DNA between the primers on the respective DNA strains are amplified selectively over the remaining portions of the DNA and selected sample. The PCR process provides for the specific amplification of a desired region of DNA.

The method of the present invention uses the PCR amplification process that allows simultaneous amplification of a "target gene", a "housekeeping" gene and competitive templates for each of these genes. According to the present invention, the terms "target DNA sequence" and "target gene" generally refer to a gene of interest for which there is a desire to selectively amplify that gene or DNA sequence. The term "housekeeping" gene refers to genes that are suitable as internal standards for amount of RNA per PCR reaction. In a general and overall sense, a key to the present invention is the simultaneous use of primers for target genes, primers for a housekeeping gene, and two internal standard competitive templates comprising mutants of the target genes and housekeeping gene. These mutations can be point mutations, insertions, deletions or the like.

There is a need for quantitative measurement of gene expression which controls for the expression of all relevant genes that may be involved in individuals at risk for certain diseases, including, for example, bronchogenic carcinoma. The present invention addresses these needs by providing a method for gene expression measurement by quantitative RT-PCR that allows simultaneous expression measurement of many genes. The multiplex competitive reverse transcriptase-poly erase chain reaction is generally described in the Willey and Willey et al. U.S. Pat. Nos. 5,639,606; 5,643,765 and 5,876,978 which are fully incorporated herein by reference, along with all other references disclosed herein and listed at the end of the specification. According to one aspect of the present invention, the mRNA expression of mGST, GSTM3, GSTT1, GSTP1, GSHPx and GSHPxA and the combined expression of GSTM1, 2, 4, 5 are simultaneously measured in the primary NBECs of non-lung cancer patients, primary NBECs from lung cancer patients, and in cultured NBECs from non-lung cancer patients.

Normal bronchial epithelial cells (NBECs) are at an increased risk for oxidative damage following inhalational exposure to reactive oxygen species in cigarette smoke (1, 2), ozone (3), possibly asbestos (4), and other particulates in the environment. NBECs also are exposed to endogenous oxidative products produced through normal cellular metabolism (5) and during inflammation (6, 7). In addition, inhaled daughters of radon-2222 decay (polonium218 and polonium214) may deposit on NBECs and emit $\alpha$ particles that generate reactive oxygen products as they encounter the cells. NBECs also are exposed through inhaled cigarette smoke or urban air pollution to polycyclic aromatic hydrocarbons (PAHs). These procarcinogens may be metabolically activated in the cytoplasm and subsequently damage nuclear DNA. Damage to NBECs and adjacent structures from oxidants and or activated carcinogens may result in a variety of pulmonary disorders, including bronchogenic carcinoma, pulmonary fibrosis, chronic bronchitis, and emphysema (5, 8).

NBECs express several enzymes, including glutathione-S-transferase (GSTs) and glutathione peroxidases, that are capable of preventing or reducing injury from reactive oxidants or carcinogens. The GST enzymes conjugate reactive chemical groups, including reactive oxygen species and diol-epoxide ultimate carcinogens, to glutathione and thereby prevent them from binding to and damaging DNA (9). There are several classes of GSTs, including one microsomal class (mGST) and four cytosolic classes: GSTA, GSTM, GSTP, and GSTT (10, 11). In addition, a human homologue of rat GSTK1 has been reported (12). Each GST enzyme has substrate specificity, but there is considerable overlap (13). For example, diol-epoxides derive from PAH procarcinogens are metabolized by GSTP1 and GSTM1-3 (14). Other substrates for the cytosolic GSTs include steroids, alkenals, and quinones (9). In contrast to the cytosolic GST enzymes, mGST has very little specificity for epoxides (15). However, mGST has activity against a broad range of other substrates, including styrene-7-8-oxide (16), 1-chloro-2,4-dinitrobenzene, and cumene hydroperoxide (17). Further, various halogenated alkynes and alkenes are metabolized preferentially by mGST compared to the cytosolic forms (13, 18).

The glutathione peroxidase enzymes catalyze the inactivation of peroxides (including hydrogen peroxide and lipid peroxides) using reduced glutathione as a cofactor (19). Several enzymes have glutathione peroxidase activity, including GSHPx (19), GSHPxA (a secreted form; Ref 20), mGST (21), GSTA (22), and GSTM3 (23).

Both intertissue and interindividual variation in the expression of GST and glutathione peroxidase genes have been reported (14, 24-27). In addition, the expression of some GST and glutathione peroxidase genes is altered in carcinoma tissues (14, 20, 24, 25, 28, 29). Because there is intertissue variation in the expression of these genes, it is important to measure expression specifically in the progenitor cell for bronchogenic carcinoma, the bronchial epithelial cell. There is very little information presently available regarding quantitative levels of GST or glutathione peroxidase gene expression in primary NBECs relative to primary bronchogenic carcinoma tissue.

The inventors herein have discovered that interindividual variation in GST enzyme gene expression translates into variation in risk for bronchogenic carcinoma. For example, in some epidemiological studies, GSTM1 null individuals have an increased risk (30, 31). However, the results of other studies are contradictory (32). One hypothesis to explain these different results is that because the multiple GST and glutathione peroxidase enzymes have a broad substrate overlap, a decrease in the expression level of one GST or glutathione peroxidase may be compensated for by increased expression of another. Thus, the expression patterns for multiple relevant GST and glutathione peroxidase enzymes may be more closely associated with risk than the expression of each individual gene. Consequently, studies that do not control for expression of all relevant genes may generate data that are difficult to interpret.

SUMMARY OF THE INVENTION

The present invention relates to a method to measure expression of multiple target genes in a progenitor cell for bronchogenic carcinoma using reverse transcription-polymerase chain reaction (RT-PCR) to allow simultaneous expression measurement of multiple target genes. The quantitative competitive RT-PCR is used to measure RNA levels of glutathione-S-transferase (GSTs) and glutathione peroxidases (GSHPxs) in the progenitor cell.

In a preferred method, at least one of the mRNA levels of the following are measured: mGST, GSTM3, combined GSTM1, 2, 4, 5, GSTT1, GSTP1, GSHPx, and GSHPxA.

The levels of GSTP1, GSTM3 and GSHPx are significantly lower in normal bronchial epithelial cell than in bronchogenic carcinoma cells. In a preferred aspect, the gene expression index is evaluated by multiplying the values for: MGSTXGSTM3XGSHPxXGSHPxAXGSTP1. The sensitivity for detecting normal bronchial epithelial cells as compared to bronchogenic carcinoma cells is about 90% and the specificity for detecting normal bronchial epithelial cells as compared to bronchogenic carcinoma cells is about 76%.

In another aspect the method comprises a) coamplifying a housekeeping gene along with the target genes (to control for the amount of cDNA included in the reaction); b) including known amounts of cDNA competitive templates (CTs) for both the target genes and the housekeeping gene (to control for the loss of predictable exponential amplification with increasing cycles); c) identifying, choosing primers for synthesizing the competitive templates (CTs) and for amplification of native template (NT) and CT sequences; d) comparing the levels of the housekeeping gene CTs to the tar get gene CTs where the ratio to housekeeping gene CT to each of the target gene CTs is the same; e) preparing a master mix (sufficient for the PCR reactions) that contains the components: dNTPs, buffer, water, Taq polymerase, cDNA and aliquot of CT solution containing known concentrations of CTs for the housekeeping gene and the target genes; f) specifying each gene to be amplified in each reaction by the primers included in each reaction by aliquoting separately from the master mix; g) determining the amount of cDNA loaded for each sample by comparing the density of PCR product band for housekeeping gene NT cDNA to PCR product band for housekeeping gene CT cDNA; and h) determining quantitative expression of the target genes.

The quantitative expression of the target genes is determined by: a) calculating a ratio of target gene NT to CT product; and b) dividing the calculated number of target gene NT molecules by the calculated number of housekeeping gene NT molecules to correct for loading differences.

The method of the present invention is especially useful for determining a patient who is at risk for developing cancer by assessing peripheral blood lymphocyte DNA for polymorphisms in a regulatory region of target genes that are associated with high or low expression of the target genes.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 1 contains Table 1 which shows the demographic data of individuals without lung cancer and individuals with cancer.

FIG. 2 contains Table 2 which shows the primer sequences (SEQ ID NOS 1-24, respectively, in order of appearance) and product lengths of both native template (NT) and competitive template (CT) PCR products.

FIG. 3 contains Table 3 which shows the GST and peroxidase gene expression (mRna/103 β-actin mRna) in primary bronchial epithelial cells from subjects withbronchogenic epithelial cells from subjects without bronchogenic carcinoma.

FIG. 4 contains Table 4 which shows the GST and peroxidase gene expression (mRNA/103 μl -actin mRNA) in primary bronchial epithelial cells from subjects with bronchogenic carcinoma.

FIG. 5 contains Table 5 which shows the GST and peroxidase gene expression (mRNA/103 β-actin mRNA) in cultured bronchial epithelial cells from subjects without bronchogenic carcinoma FIG. 6 contains Table 6 which shows gene expression test to identify NBECs from subjects with bronchogenic carcinoma.

FIG. 7 shows representative agarose gels.

FIG. 8 shows glutathione peroxidase (A) or index values (B-E) for NBEC samples.

DETAILED DESCRIPTION OF THE INVENTION

For many years, gene expression has been measured through quantification of RNA By Northern or dot blot analysis. These techniques require the amount of RNA obtainable from at least 1 cells for each measurement. Often, a biopsy will provide only the number of cells necessary for a histological diagnosis and this is often far less than $10^5$ cells. Recently developed PCR techniques allow measurement of RNA levels in as few as 100 cells. However, techniques described thus far allow only qualitative, not quantitative measurement.

The present invention uses the using multiplex competitive reverse-transcriptase polymerase chain reaction amplification to simplify and improve quantitative measurement of gene expression as described in U.S. Pat. No. 5,876,978 to Willey et al. DNA extracted from samples is reverse transcribed and then subjected to PCR amplification in the present of primers for both a "housekeeping" gene and targets gene of interest.

The amount of a target DNA sequence is quantified within an identified region of a selected cDNA molecule that is present within a heterogeneous mixture of cDNA molecules. It is to be understood that more than one targeted gene and/or housekeeping gene can be utilized and further that quantitation of such additional target and/or housekeeping genes will necessitate the further inclusion of an internal standard competitive template comprising a mutation of that additional target and/or housekeeping gene. It is to be understood that the mutated competitive templates comprise at least one nucleotide that is mutated relative to the corresponding nucleotide of the target sequence. It is to be noted that mutation of only a single nucleotide that is complementary to the corresponding nucleotide of the housekeeping gene sequence is required for the successful practice of the present invention. However, it is understood that longer deletions, insertions or alternations are useful in the present invention. The target gene primers (which serve as primers for both the native and competitive templates of the target gene), housekeeping gene primers (which serve as primers for both the native and competitive template of the housekeeping gene), competitive templates of the target genes, and competitive template of the housekeeping gene are subject to a PCR process along with native cDNA which contains the DNA for both the target genes and the housekeeping gene. The PCR process provides cDNA products of 1) native cDNA of the target genes and the housekeeping gene and 2) mutated competitive templates cDNA of the target genes and the housekeeping gene. The cDNA products are isolated using methods suitable for isolating cDNA products. The relative presence of the native cDNA products and the mutated cDNA products are detected by measuring the amounts of native cDNA coding for the target gene and mutated coding for the competitive template of the target gene as compared to the amounts of native cDNA coding for the housekeeping gene and mutated cDNA coding for competitive template of the housekeeping gene.

The terms primers, nucleic acids and oligonucleotides are understood to refer to polyribonucleotides and polydeoxyribonucleotides and there is no intended distinction in the length of sequences referred to by these terms. Rather, these terms refer to the primary structure of the molecule. The terms include double and single stranded RNA and double and single stranded DNA. It is to be understood that the oligonucleotides can be derived from any existing or natural sequence and generated in any manner. It is further understood that the oligonucleotides can be generated from chemical synthesis, reverse transcription, DNA replication and a combination of these generating methods. The term "primer" generally refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in suitable a buffer which may include constituents which are co-factors or which affect conditions such as pH and the like at various suitable temperatures. It is understood that while a primer is preferably a single strand sequence, such that amplification efficiency is optimized, other double stranded sequences can be practiced with the present invention.

The terms "target gene", "sequence" or "target nucleic acid sequence" are meant to refer to a region of an oligonucleotide which is either to be amplified and/or detected. It is to be understood that the target sequence resides between the primer sequences used to the amplification process.

The quantitative gene expression is measured by multiplex competitive PCR amplification of a) cDNA from at least one target gene of interest an at least one "housekeeping" gene and b) internal mutated standard competitive templates comprising base mutants of the target gene of interest and the "housekeeping" gene cDNA that causes either a loss or gain of a restriction endonuclease recognition site. The method comprises the PCR amplification of a) cDNA from at least one target gene of interest and at least one "housekeeping" gene and b) competitive templates comprising sequences of the target gene of interest and the "housekeeping" gene that have been artificially shortened. These shortened sequences retain sequences homologous to both the target gene and the housekeeping gene primers used in PCR amplification. RNA extracted from sample cells or tissues are reverse transcribed. Serial dilutions of cDNA are PCR amplified in the presence of oligonucleotides homologous to the target gene and the "housekeeping" gene, and quantified amounts of internal mutated standard competitive templates. The amplified DNA is restriction digested and electrophoresed, separating native from mutated products. Densitometry is performed to quantify the bands. This technique to measure the relative expression of a target gene to a "housekeeping" gene is precise and reproducible for studies done with the same master mixture and dilution of internal standards.

Synthesized oligonucleotides homologous to any sequences containing a known restriction endonuclease recognition site or any sequence containing one or two-base pair mismatch for a known restriction endonuclease site that is present in the housekeeping gene can be utilized. The application of these restriction endonuclease recognition sites is to either mutate the naturally occurring sites to non-recognition sites or to mutate the mismatch sites to match sites, in either case creating mutant sequences suitable for internal mutated standards competitive templates. The particular sites in the housekeeping gene used for analysis of any particular other gene depends on the match and mismatch sites that are present in the other gene. One determinant is the size of the DNA fragments that are generated from the housekeeping gene and the target gene. It is desired that these fragments separate well on gel electrophoresis.

Further, all oligonucleotides that contain sequences homologous to sequences in the genes for the housekeeping genes can be used in the present invention. Such homologous sequences may be used to generate artificially shortened competitive templates to the housekeeping genes generated according to the method described in the Willey et al. U.S. Pat. No. 5,576,978.

To identify and match one or two base mismatch sequences for all known recognition sites, it is possible to use the Map program within the Genetics Computer Group software package (Devereux et al., supra. 1984). The cDNA sequences are obtained for each gene, then each gene is evaluated for the presence of the match of one or two base pair mismatch sequences for every known restriction endonuclease. It is possible to use every gene containing any of these recognition sequences or one or two base pair mismatches of these sequences.

Multiplex competitive PCR improves and simplifies quantitation of gene expression. Gene expression can be quantitated in very small samples of tissue or cells without resorting to radio labeling. As a result, multiplex reverse transcription PCR is less expensive and safer to use than radio labeling. The results are reproducible for examples using the same master mixture and dilutions of internal mutated standard competitive templates.

It is to be understood that all oligonucleotides homologous to each strand of the cDNA of known or potential housekeeping genes (including but not restricted to the human, mouse and rat GAPDH, β-actin, 28S RNA, 18S RNA, and all ribonucleic protein genes) and containing restrictions endonuclease recognition sites sequences or one or two base pair mismatches for restriction endonuclease recognition sequences are useful in the practice of the present invention. The oligonucleotides are used to prepare competitive templates of housekeeping genes for use in quantitative PCR.

It is to be further understood that according to the method of the present invention, all oligonucleotides that contain sequences homologous to sequences in known or potential housekeeping genes (including but not restricted to GAPDH, β-actin, 28S RNA, 18S RNA, and all ribonucleic protein genes) are useful in generating artificially shortened competitive templates. The oligonucleotides are used to prepare competitive templates of housekeeping genes for use in the present invention It is contemplated that uses of this inventive technique include: a) evaluating gene expression from tissues obtained by endoscopic biopsy (brush or forceps), needle aspiration, and bone marrow biopsy; b) quantification of reporter gene expression in transient transfection assays; and c) quantification of transfected genes following gene therapy.

It should be further understood that according to the method of the present invention, more than one gene can be evaluated at the same time to determine the interindividual variation in antioxidant gene expression that results in interindividual variation in risk for bronchogenic carcinoma.

Three genes, GSTM3, GSHPx, and GSTP1, are expressed at lower levels in NBECs from lung cancer patients compared to NBECs from individuals without lung cancer. Because GSHPx and GSTM3 each have peroxidase activity, cells expressing low levels of these genes are more susceptible to oxidant damage and carcinogenic transformation. Further, GSTM3 and GSTP1 metabolically inactivate PAH diol-epoxide carcinogens in NBECs; thus, decreased expression levels in NBECs lead to a decrease in the cellular capacity to detoxify these carcinogens. It has been reported that decreased expression of mouse GST.π may be responsible for the increased carcinogenicity of the PAH benzo(a)pyrene (41). GSTP1 was expressed at a higher level in NBECs from non-lung cancer patients than the other genes studied-herein. Recently described polymorphisms in the coding region of GSTP1 have a strong association with increased risk for neoplasia (42, 43) and are important to assess along with GSTP1 gene expression levels.

Although ~50% of Caucasians lack GSTM1 expression due to a null allele, NBECs from all 34 patients in this study expressed one or more of these GSTM isoforms (See FIGS. 3 and 4). Because all of the GSTM isoforms have substrate overlap, it is possible that risk for bronchogenic carcinoma is not related to GSTM1 expression alone but also to relative gene expression levels of all GSTM isoforms in NBECs.

Non-cancer subjects 21 and 54 had mGST levels three logs and 10-fold greater, respectively, than any of the other subjects. Such wide fluctuation in gene expression was not observed for any of the other genes. It is possible that a small segment of the population is capable of expressing very high levels of mGST either constitutively or upon exposure to certain xenobiotics. Because mGST has peroxidase activity (21) and because it was expressed at lower levels in the NBECs of lung cancer patients in this study (Tables 3 and 4), it would be expected that such a high level of expression would protect the cellular DNA from oxidant damage and therefore lower cancer risk. The reason that mGST expression is not significantly different in the two groups, although there is a 5-fold difference in the means, is that the subject 54 value confers such a high SD. If both subjects 21 and 54 are excluded from analysis, mean mGST expression is significantly lower ($P<0.05$) in the samples from cancer patients.

Although protein and/or enzyme levels were not measured, mRNA levels and enzyme activities for some of the measured genes and other xenobiotic metabolism enzyme genes are known to be closely related. For example, Mosco et al. (44) reported in 1988 that GSTP1 enzyme activity and mRNA levels are highly correlated in several human breast cancer cell lines. We have reported previously that CYP1A1 and NADPH oxidoreductase activities are correlated with mRNA levels in lymphoblastoid cell lines (35). CYP1A1 mRNA and enzyme activities also have been correlated in rat liver tissue (45). Further, manganese superoxide dismutase activity correlates with protein and mRNA levels in fibroblasts (46).

Gene Expression Indices Identifies Individuals at Risk for Bronchogenic Carcinoma.

An important feature of the method of the present invention is that it allows expression values of multiple different genes to be combined into indices. Such index values are used to rank cell or tissue samples. The gene expression indices generally correlate better than expression of any single gene or isozyme and phenotype. For the best index identified (mGST×GSTM3×GSHPx×GSHPxA×GSTP1) at a value that provided a sensitivity of ≥90%, the specificity was 76% (Table 6). Because 5-10% of smokers get lung cancer, it is reasonable to hypothesize that at least 5-10% of the people in the general population have a genetic predisposition to bronchogenic carcinoma. Thus, of the four individuals without bronchogenic carcinoma who had index values below the cutoff value, one to two of them could be expected to be at high risk for bronchogenic carcinoma if they smoked.

The manner in which gene expression values are combined into indices depends in part on the weight given each gene. Indices are calculated by multiplying gene expression values together so that each gene expression value included has equal weight. One assumption made is that, at the mean level of expression measured in NBECs, each of the genes studied contributes equally to protection of NBECs from oxidant an or carcinogen damage. This assumption is supported by the expectation that the optimal level of expression for the function of each gene would be selected for through evolution. By combining gene expression values into indices in a previous study (36) of bronchial epithelial cells, it is now possible to identify a gene expression index that is highly correlated with bronchogenic carcinoma by empirically combining multiple cell cycle gene expression values. This method is useful for combining individual gene expression values into indices to better define the mechanisms underlying cellular phenotype.

Environmental Exposures Aspect Antioxidant Gene Expression.

The observed interindividual variation in the expression of GST and GSHPx enzyme genes in primary NBECs (Tables 3 and 4) may result from several different factors, including variation in constitutive level of gene expression, variation in the inducible level of gene expression and variation in inhalational exposure to exogenous oxidants, and xenobiotics in the form of cigarette smoke, occupational, or environmental pollutants. Although no significant relationship between antioxidant gene expression and present smoking or amount of past smoking (in pack-years) was observed, it remains possible that the interindividual variation in gene expression observed could be due to variation in exposure to xenobiotics and/or oxidants from sources other than cigarette smoke.

Lower mean antioxidant gene expression and interindividual variation in expression among the cultured cells support the theory that the variation observed among the primary NBECs is at least in part due to environmental rather than hereditary causes. Further, it is possible that hereditary differences caused variation in inducible as well as constitutive levels of the genes tested. Thus, the NBECs of cancer patients may express lower levels of GSTM3, GSHPx, and GSTP1 due to the inheritance of particular polymorphisms in the regulatory regions of these genes or of the transcription factors that bind to them.

EXAMPLE

Materials and Methods

Reagents. 10×PCR buffer [500 mM Tris (pH 8.3), 2.5 mg/µl BSA, 30 mM MgCl2] was obtained from Idaho Technology, Inc. (Idaho Falls, Id.). Taq polymerase (5 units/µl), oligo dT primers, Rnasin (25 units/µl), pGEM size marker, and dNTPs were obtained from Promega (Madison, Wis.). Moloney murine leukemia virus reverse transcriptase (200 units/µl), 5× first strand buffer [250 mM Tris-HCl (pH 8.3), 375 mM KCl, 15 mM MgCl2, 50 mM DTT], and RNase-free water were obtained from Life Technologies, Inc. (Gaithersburg, Md.), NuSieve and SeaKem LE agarose were obtained from FMC BioProducts (Rockland, Me.). TriReagent was obtained from molecular Research Center (Cincinnati, Ohio), Bronchial epithelial cell growth medium was obtained from Clonetics (San Diego, Calif.). Natural human fibronectin and collagen (type I rat tail) were obtained from Collaborative Biomedical Products (Bedford, Mass.), All other chemicals and reagents were molecular biology grade.

Samples. Primary NBECs were obtained by bronchial brush biopsy as previously reported (34, 35). This group of individuals without lung cancer consisted of healthy volunteers from a university setting, individuals under going diagnostic bronchoscopy, and three organ donors. The lungs of the donors did not meet criteria for transplantation due to COPD (subjects 54 and 62) or asthma (subject 55). Two of the subjects (57 and 71) had bronchoscopy at the time of thoracotomy for resection of adenocarcinoma of the colon that had metastasized to the lung. Subjects 59 and 63-66 had bronchoscopy due to persistent hemoptysis or change in character of chronic cough, and no endobronchial mucosal lesions were observed. Samples from lung cancer patients were obtained via bronchoscopic bronchial brushing at the time of surgery as previously reported (36) or brushing of surgically resected samples (subjects 74 and 75; Table 1). Samples that were evaluated in previous studies (34, 35) have the same subject numbers in this study. Samples acquired since the time of those publications are numbered in order of acquisition. Cells were recovered from the bronchial brush into ice-cold 0.9% NaCl solution and pelleted. Informed consent was obtained from each patient. Demographic data are presented in Table 1.

RNA Extraction and Reverse Transcription. Excess NaCl solution/media was removed, and the cells were lysed in TriReagent. Total RNA was extracted according to the TriReagent Manufacturer Protocol (37). Following extraction, mRNAs were reverse-transcribed using M-MLV reverse transcriptase and an oligo dT primer as previously reported (34).

Quantitative RT-PCR. Gene expression was determined using quantitative competitive RT-PCR (33-35, 38). PCR reactions were cycled 35 "N" in a Rapidcycler (Idaho Technology, Idaho Falls, Id.) in the presence of two types of controls. First, a housekeeping gene (β-actin) was coamplified along with the target genes to control for the amount of cDNA included in the reaction. Second, known amounts of cDNA CTs were included for both the target and the housekeeping gene to control for the loss of predictable exponential amplification with increasing cycles (38, 39). In these experiments, the concentration of the CTs in each PCR reaction was $10^{14}$ $^{-}$M for β-actin and varied for each of the other genes, CTs were synthesized according to previously described methods (33, 40). Primers for synthesizing CTs and for amplification of NT and CT sequences were chosen using Oligo software (National Biosciences, Inc., Plymouth, Minn.). After careful assessment of the sequences, we were not able to identify primers what would amplify GSTM1 without amplifying GSTM2, 4, 5. Therefore, cDNA from all four isogenes were amplified with the same primers. Sequences for mGST (GenBank accession no. J03746) (Forward: Seq. ID No. 22; Reverse: Seq. ID No. 23; CT: Seq. ID No. 24), GSTM3 (J05459) (Forward: Seq. ID No. 13; Reverse. Seq. ID No. 14; CT: Seq. ID No. 15), GSTM1, 2, 4, 5 (J03817, M63509, M96234, L02321) (Forward: Seq. ID No. 10; Reverse: Seq. ID No. 11; CT: Seq. ID No. 12), GSTT1 (X79389) (Forward: Seq. ID No. 19; Reverse: Seq. ID No. 20; CT: Seq. ID No. 21), GSHPx (Y00433) (Forward: Seq. ID No. 4; Reverse: Seq. ID No. 5; CT: Seq. ID No. 6), GSHPxA (D00632) (Forward: Seq. ID No. 7; Reverse: Seq. ID No. 8; CT: Seq. ID No. 9), and GSTP1 (X06547) (Forward: Seq. ID No. 16; Reverse: Seq. ID No. 17; CT: Seq. ID No. 18) were retrieved from GenBank. Table 2 lists primer sequences and product lengths for both NT and CT PCR products. Primers for β-actin (Forward: Seq. ID No. 1; Reverse: Seq. ID No. 2; CT: Seq. ID No. 3) have been reported previously (34).

In each experiment, all of the genes were evaluated in a single sample. Three stock mixtures of CTs were prepared, and these same three stocks were used for each experiment. Levels of housekeeping and target gene CTs in the separate CT mixes were compared to each other. Thus, the ratio of the housekeeping gene CT to each of the target gene CTs was the same when each sample was assessed. For each experiment, a master mix sufficient for the planned number of PCR reactions was prepared that contained every component except the primers. The components of the master mix were dNTPs, buffer, water, Taq polymerase, cDNA, and an aliquot of CT solution. The CT solution contained known concentrations of CTs for the housekeeping gene and the target genes. The gene to be amplified in each reaction was specified by the primers included in each reaction tube, aliquoted separate from the master mix. Whenever possible, triplicate experiments were performed.

The amount of cDNA loaded for each sample was determined by comparing the density of the PCR product band for β-actin CT cDNA. Quantification of expression of the target genes was determined in the following way. First, the ratio of target gene native template:competitive template (NT:CT) product was calculated. Because the starting target gene CT concentration was known and the relative simplification efficiencies for the NT and CT cDNAs were known (see below), the starting target gene NT cDNA concentration could be determined. Second, the calculated number of target gene NT molecules was divided by the calculated number of β-actin NT molecules to correct for loading differences. Gene expression values are reported in Tables 3, 4 and 5.

Visualization and Quantification. After amplification, products were electrophoresed on 4% agarose gels (3:1 NuSieve:SeaKem) containing 0.5 µg/ml ethidium bromide. Gels were visualized with a Foto/Eclipse image analysis system (Fotodyne, Hartland, Wis.), and digital images were saved on a Power Mac 7100/66 computer as previously described (34). Collage software (Fotodyne) was used for densitometric analysis. A representative gel is seen in FIG. 7.

Statistical Analysis. A Student's t test was used to investigate statistical differences between primary NBECs from non-lung cancer patients and primary NBECs from lung cancer patients for each gene or gene expression index. The Student's t test also was used to assess for significant differences in the expression value of any gene or gene expression index due to gender. A two-factor ANOVA followed by a Duncan's Multiple Range Test was used to determine statistically significant differences in gene expression levels and gene expression index values between present smokers, former smokers, and never smokers. A Pearson's correlation was used to determine whether there was a statistical association between the expression value for each gene or gene expression index with amount of past smoking (in pack-years). The relationship between gene expression and age was assessed by the same method. All of Pearson's correlation tests were assessed for all individuals, only lung cancer patients, only non-lung cancer patients, only present smokers, and only former smokers. $X^2$ analysis was conducted for each gene or gene expression index using a range of cutoff values to determine their sensitivity and specificity as a test for separating cancer patients from non-lung cancer patients (Table 6). To determine statically significant (P<0.05) interindividual variation in gene expression levels among primary NBECs from non-lung cancer patients and primary NBECs from lung cancer patients and compare this variation with interindividual variation in cultured NBECs, a one-factor ANOVA was used. All statistical analyses were conduced using SAS version 6.11 (SAS Institute, Cary, N.C.).

At least three replicate measurements were done for each gene expression assessment when sufficient cDNA was available. Of the 280 gene expression means reported in Tables 3, 4, and 5, three or more replicate measurements were made for 218, and an SD is provided. Of the remaining 62 gene expression means reported, duplicate measurements were obtained for 48, and a range is provided. There was sufficient cDNA for only one measurement for 14 gene expression values.

Results

Reproducibility. Among the gene expression measurements for which three or more replicate values were obtained, the SD was <50% of the means for 149 of 218, <75% for 190 of 218, and <100% for 210 of 218, with the SD >100% of the mean for 8 of 218 expression measurements (Tables 3, 4, and 5). This is similar to the reproducibility observed in other gene expression studies using the same method (33).

Comparison of Primary NBECs from Individuals with or without Bronchogenic Carcinoma Individual Gene Expression Values. GSTM3, GSTP1, and GSHPX were expressed at significantly lower levels (P=0.02, 0.01, and 0.01, respectively) in primary NBECs from bronchogenic carcinoma patients compared to primary NBECs from individuals without bronchogenic carcinoma (bold font in Table 4). Of these genes, GSHPx was the individual gene with the best sensitivity (80% for a value of 70-90 mRNA/103 µ-actin mRNA; Table 6). However, a value that was >90% sensitive had poor specificity (FIG. 8A).

For the other four genes tested, no significant difference in gene expression between the two groups of primary NBECs was observed.

Gene Expression Indices. Indices comprising expression values of multiple genes were formed by multiplying expression values of different combinations of genes together. Rather than assessing every possible combination of genes, 25 indices comprising the 5 genes that individually demonstrate the greatest difference between groups (GSP1, GSH-PxA, GSTM3, mGST, and GSHPx; Table 6) were assessed. Index values were reported as molecules/$10^3$ molecules of β-actin and were calculated as the following example; (GSTM3 molecules/$10^3$ molecules of β-actin×GSTP1 molecules/$10^3$ molecules of β-actin×mGST molecules/$10^3$ molecules of β-actin=GSTM3×GSTP1×mGST molecules/$10^9$ molecules of β-actin/$10^6$ molecules of β-actin-index molecules/$10^3$ molecules of β-actin.

For two indices that each comprised three genes (GSTP133 GSHPx ×GSTM3; GSTP1×mGST×GSHPx), it was possible to identify cutoff values with sensitivities ≥90% and specificities >70% (Table 6; FIGS. 8, B and C). These indices both included GSTP1 and GSHPx and varied only with respect to the third gene (either mGST or GSTM3). For an index that included all four of these genes (mGST×GSTM3×GSHPx× GSTP1), a range of cutoff values ($3.2 \times 10^5$ –$3.5 \times 10^{-5}$ molecules/$10^3$ molecules of β-actin) had a sensitivity of 100%. However, the specificity of this index was only 62% (Table 6). Reducing the cutoff value to $2.0 \times 10^{-5}$ molecules/$10^3$ β-actin decreased the sensitivity to 90% but did not improve the specificity (FIG. 8D). In addition, for an index comprising five genes (mGST×GSTM3×GSHPx×GSHPxA×GSTP1), a range of cutoff values ($3.0 \times 10^9$ –$1.0 \times 10^{8\ l\ molecules/}10^3$ molecules of β-actin) had a sensitivity of 90% and a specificity of 76% (Table 6; FIG. 8E).

Correlation with Age, Gender, and Smoking Age. Pearson's correlation was used to test the relationship of age to the expression of each gene and the level of each gene expression index. First, the test was run on all patients. Only GSHPx was significantly associated (negatively correlated) with age (P=0.018). To avoid bias caused by the relatively low representation of older individuals in the non-lung cancer group (mean age among non-lung cancer and lung cancer patients was 39 and 69 years, respectively), the test also was run separately on the lung cancer patients and the non-lung cancer patients. There was no significant association within either the non-lung cancer or the lung cancer group between age and GSHPx. GSHPx gene expression also was assessed separately on samples from individuals aged 45-65 years. In this group, the mean age among nine non-lung cancer and four lung cancer individuals was 54 and 55 years, respectively. As with the entire group, the mean level of GSHPx expression among the cancer cases (35.9 molecules/$10^3$ molecules of β-actin) was significantly lower (P=0.01) than the mean GSHPx expression among non-lung cancer cases (122 molecules/$10^3$ molecules of β-actin).

Smoking History. A Pearson's correlation was used to assess relationships between smoking history and gene expression. This test was run once on all patients, once on present and former smokers only, once on present smokers only, and once on former smokers only. No correlation between expression of any gene or gene expression index studied here with smoking history (in pack-years) was observed among patients of any group.

Gender. Among the primary NBECs from lung cancer and non-lung cancer patients combined, no differences in gene expression or any gene expression index were found due to gender.

Interindividual Variation in Gene Expression

Primary NBECs. There was significant (P<0.05) interindividual variation in primary NBEC expression of each of the genes (Tables 3 and 4). The value of mGST in NBECs from subject 21 was excluded from statistical analysis because it was an outlier (Table 3). Interpretation of this result is included in the discussion.

Cultured NBECs. In an effort to test whether the interindividual variation in expression observed in primary NBECs was based on hereditary differences or environmental factors, gene expression was measured in cultured NBECs from eight different individuals with no history of lung cancer. All of the cultures were maintained under the exact same conditions. This allowed hereditary differences in constitutive gene expression to predominate. In these eight different NBEC cultures, the mean level of expression for each antioxidant gene studied was lower than that observed among primary NBEC samples. In addition, although significant interindividual variation among cultured NBECs was observed for GSHPx, GSTM3, and mGST, it was less than that observed in primary NBECs (Tables 3, 4, and 5). Further, there was no significant interindividual variation in the expression of GSTM1, 2, 4, 5, GSTT1, GSHPxA, or GSTP1 among cultured NBECs (Table 5).

The present invention involves a dramatic improvement over previously described approaches for evaluating interindividual aeration in risk for damage to normal bronchial epthiothial cells.

REFERENCES

1. Church, D. F., and Pryor, W. A. Free-radical chemistry of cigarette smoke and its toxicological implications. Environ. Health Perspect., 64:111-126, 1985.
2. Niki, E., Minamisawa, S., Oikawa, M., and Komuro, E. Membrane damage from lipid oxidation induced by free radicals and cigarette smoke. Ann. NY Acad. Sci., 686:29-37, 1993
3. Frampton, M. W., Samet, J. M., and Utell, M. J. Environmental factors and atmospheric pollutants. Semin. Respir. Infect., 6:185-193, 1991.
4. Anttila, S., Luostarinen, L., Hirvonen, A., Elovaara, E., Karjalainen, A., Nurminen, T., Hayes, J. D., Vainio, H., and Ketterer, B. Pulmonary expression of glutathione S-transferase M3 in lung cancer patients: Association with GSTM1 polymorphism, smoking, and asbestos exposures. Cancer Res., 55:3305-3309, 1995.
5. Quinlan, T., Spivack, S., and Mossman, B. T. Regulation of antioxidant enzymes in lung after oxidant injury. Environ. Health Perspect., 102:79-87, 1994.
6. Avissar, N., Finkelstein, J. N., Horowitz, S., Willey, J. C., Coy, E., Frampton, M. W., Watkins, R. H., Khullar, P., Xu, Y., and Cohen, H. J. Extracellular glutathione peroxidase in human lung epithelial lining fluid and in lung cells. Am. J. Physiol., 270:L173-L182, 1996.
7. Borm, P. J. A., and Driscoll, K Particles, inflammation and respiratory tract carcinogenesis. Toxicol. Lett. (Amst.), 88:109-113, 1996.
8. Cantin, A., and Crystal, R. G. Oxidants, antioxidants and the pathogenesis of emphysema. Eur. J. Respir. Dis. Suppl., 139:7-17, 1985.
9. Mannervik, B., and Danielson, U. H. Glutathione transferases—structure and catalytic activity CRC Crit. Rev. Biochem., 23:283-337, 1988
10. Mannervik, B., Alin, P., Guthenberg, C., Jensson, H., Tahir, M. K., Warholm, M., and Homvall, H. Identification of three classes of cytosolic glutathione transferase common to several mammalian species: correlation between structural data and enzymatic properties. Proc. Natl. Acad. Sci. USA, 82:7202-7206, 1985.
11. Meyer, D. J., Coles, B., Pemble, S. E., Gilmore, K. S., Fraser, G. M., and Ketterer, B. θ, a new class of glutathione transferases purified from rat and man. Biochem. J., 274:409414, 1991.
12. Pemble, S. E., Wardle, A. F., and Taylor, J. B. Glutathione S-transferase class K: characterization by the cloning of rat mitochondrial GST and identification of a human homologue. Biochem. J., 319:749-754, 1996.
13. Hayes, J. D., and Pulford, D. I. The glutathione S-transferase supergene family: regulation of GST* and the contribution of the isoenzymes to cancer chemoprotection and drug resistance. Crit. Rev. Biochem. Mol. Biol., 30:445-600, 1995.
14. Antilla, S., Hirvonen, A., Vainio, H., Husgafvel-Pursiainen, K., Hayes, J. D., and Ketterer, B. Immunohistochemical localization of glutathione S-transferases in human lung. Cancer Res., 53:5643-5648, 1993.
15. Morgenstem, R., Lundqvist, G., Hancock, V., and DePierre, J. W. Studies on the activity and activation of rat liver microsomal glutathione transferase, in particular with a substrate analogue series. J. Biol. Chem., 263:6671-6675, 1988.
16. Strange, R. C., Matharoo, B., Faulder, G. C., Jones, P., Cotton, W., Elder, J. B., and Deakin, M. The human glutathione S-transferases; a case-control study of the incidence of the GST10 phenotype in patients with adenocarcinoma. Carcinogenesis (Lond.), 12:25-28, 1991.
17. Tsuchida, S., and Sato, K. Glutathione transferases and cancer. Crit. Rev. Biochem. Mol. Biol., 27:337-384, 1992.
18. Anderson, C., Mosialou, E., Weinander, R., and Morgenstern, R. Enzymology of microsomal glutathione S-transferase. Adv. Pharmacol., 27:19-35, 1994.
19. Takahashi, K., Akasaka, M., Yamamoto, Y., Kobayashi, C., Mizoguchi, J., and Koyama, J. Primary structure of human plasma glutathione peroxidase deduced from cDNA sequences. J. Biochem., 108:145-148, 1990.
20. Chu, F., Esworthy, R. S., Doroshow, J. H., Doan, K., and Liu., X. Expression of plasma glutathione peroxidase in human liver in addition to kidney, heart, lung, and breast in humans and rodents. Blood, 79:3233-3238, 1992
21. Morgenstern, R., and DePierre, J. W. Membrane-bound glutathione transferase. Biochem. Soc. Trans., 15:719-721, 1987.
22. Singhal, S. S., Gupta, S., Ahmad, H., Sharma, R., and Awasthi, Y. C. Characterization of a novel α-class anionic glutathione S-transferase isozyme from human liver. Arch. Biochem. Biophys., 279:45-53, 1990.
23. Comstock, K. E., Widersten, M., Hao, X. Y., Henner, W. D., and Mannervik, B. A comparison of the enzymatic and physicochemical properties of human glutathione transferase M4-4 and three other human Mu class enzymes. Arch. Biochem. Biophys., 311:487-495, 1994.
24. Kano, T., Sakai, M., and Muramatsu, M. Structure and expression of a human class 7 glutathione S-transferase messenger RNA. Cancer Res., 47:5626-5630, 1987.
25. Tsuchida, S., Sekine, Y., Shineha, R., Nishihira, T., and Sato, K. Elevation of the placental glutathione S-transferase form (GST-π) in tumor tissues and the levels in sera of patients with cancer. Cancer Res., 49:5225-5229, 1989.
26. Mosco, J. A., Fairchild, C. r., Madden, M. J., Ransom, D. T., Wieand, H. S., O'Brien, E. E., Poplack, D. G., Cossman, J., Myers, C. E., and Cowan, K. H. Expression of anionic glutathione S-transferase and P-glycoprotein genes in human tissues and tumors. Cancer Res., 49:1422-1428, 1989.
27. Ketterer, B., Harris, J. M., Talaska, G., Meyer, D. J., Pemble, S. E., Taylor, J. B., Lang, N. P., and Kadlubar, F. F. The human glutathione 5-transferase supergene family, its polymorphism, and its effects on susceptibility to lung cancer. Environ. Health Perspect., 98:87-94, 1992.

28. Mannervik, B., Castro, V., Danielson, U. H., Platz, A., Mansson, J., and Ringbong, U. Expression of class πglutathione transferase from drug-resistant human melanoma cells. Proc. Am. Assoc. Cancer Res., 28:19, 1987.
29. Howie, A. F. Forrester, L. M., Glancey, M. J., Schlager, J. J., Powis, G., Beckett, G. J., Hayes, J. D., and Wolf, C. R. Glutathione S-transferase and glutathione peroxidase expression in normal and tumour human tissues. Carcinogenesis (Lond.), 11:451-458, 1990
30. Seidegard, J., Pero, R. W., Markowitz, M. M., Roush, C., Miller, D. G., and Beattie, E. J. Isoenzyme(s) of glutathione transferase (class Mu) as a marker for the susceptibility to lung cancer: a follow up study. Carcinogenesis (Lond.), 11:33-36, 1990
31. Nazar-Stewart, V., Motulsky, A. C., Eaton, D. L., White, E., Hornung, S. K, Leng, Z., Stapleton, P I., and Weiss, N. S. The glutathione S-transferase mu polymorphism as a marker for susceptibility to lung carcinoma. Cancer Res., 53:2313-2318, 1993.
32. Zhong, S., Howie, A. F., Ketterer, B., Taylor, J., Hayes, J. D., Beckett, C. J., Wathen, C. G., Wolf, C. R., and Spurr, NT. K. Glutathione S-transferase mu locus: use of genotyping and phenotyping assays to assess association with lung cancer susceptibility. Carcinogenesis (Lond.), 12:1533-1537, 1991.
33. Willey, J. C., Crawford, E. L., Jackson, C. M., Weaver, D. A., Hoban, J. C., Khuder, S. A., and DeMuth, J. P. Expression measurement of many genes simultaneously by quantitative PT-PCR using standardized mixtures of competitive templates. Am. J. Respir. Cell Mol. Biol., 19:6-17, 1998.
34. Willey, J. C., Coy, E., Brolly, C., Utell, M. J., Frampton, M. W., Hammersley, J., Thilly, W. G., Olson, D., and Cairns, K. Xenobiotic metabolism enzyme gene expression in human bronchial epithelial and alveolar macrophage cells. Am. J. Respir. Cell Mol. Biol., 14:262-271, 1996.
35. Willey, J. C., Coy, E. L., Frampton, M. W., Tones, A., Apostolakos, M. J., Hoehn, G., Schuermann, W. H., Thilly, W. C., Olson, D. E., Hammersley, J. R., Crespi, C. L., and Utell, M. J. Quantitative RT-PCR measurement of cytochromes p450 1A1, 1B1, and 2B7, microsomal epoxide hydrolase, and NADPH oxidoreductase expression in lung cells of smokers and non-smokers. Am. J. Respir. Cell Mol. Biol., 17:114-124, 1997.
36. DeMuth, J. P., J. P., Jackson, C. M., Weaver, D. A., Crawford, E. L., Durzinsky, D. S., Durham, S. J., Zaher, A., Phillips, E. R., Khuder, S. A., and Willey, J. C. The gene expression index c-mdcyXE2F-1/p21 is highly predictive of malignant phenotype in human bronchial epithelial cells. Am. J. Respir. Cell Mol. Biol., 19:18-24, 1998.
37. Chomczynski, P. A reagent for the single-step simultaneous isolation of RNA, DNA and proteins from cell and tissue samples. Anal. Biochem., 162:156-159, 1993.
38. Apostolakos, M. J., Schuermann, W. H. T., Frampton, M. W., Utell, J. J., and Willey, J. C. Measurement of gene expression by multiplex competitive polymerase chain reaction. Anal. Biochem., 213:277-284, 1993.
39. Gilliland, C., Perrin, S., Blanchard, K., and Bunn, H. F. Analysis of cytokine mRNA and DNA: Detection and quantification by competitive polymerase chain reaction. Proc. Natl., Acad. Sci., USA, 87:2725-2729, 1990.
40. Celi, F. S., Zenilman, M. E., and Shuldiner, A. R. A rapid and versatile method to synthesize internal standards for competitive PCR. Nucleic Acids Res., 21:1047, 1993
41. Sharma, R., Haque, A. K., Awasthi, S., Singh, S. V., Piper, J. T., and Awasthi, Y. C. Differential carcinogenicity of benzo[a]pyrene in male and female CD-1 mouse lung. J. Toxicol. Environ. Health, 52:45-62, 1997.
42. Harries, L. W., Stubbins, M. J., Forman, D., Howard, G. C., and Wolf, C. R. Identification of genetic polymorphisms at the glutathione S-transferase πlocus and association with susceptibility to bladder, testicular and prostate cancer. Carcinogenesis (Lond.), 18:641-644, 1997.
43. Ryberg, D., Skaug, V., Hewer, A., Phillips, D. H., Harries, L. W., Wolf, C. R., Ogreid, D., Ulvik, A., Vu, P., and Haugen, A. Genotypes of glutathione transferase M1 and P1 and their significance for lung DNA adduct levels and cancer risk, Carcinogenesis (Lond.), 18:1285-1289, 1997.
44. Moscow, J. A., Townsend, A. J., Goldsmith, M. E., Whang-Peng, J. Vickers, P. J., Poisson, R., Legault-Poison, S., Myers, C. E., and Cowan, K. H. Isolation of the human anionic glutathione S-transferase cDNA and the relation of its gene expression to estrogen-receptor content in primary breast cancer. Proc. Natl. Acad. Sci. USA, 85:6518-6522, 1988.
45. Heuvel, J. P. V., Clark, G. C., Kohn, M. C., Tritscher, A. M., Greenlee, W. F., Lucier, G. W., and Bell, D. A. Dioxin-responsive genes: examination of dose-response relationships using quantitative reverse transcriptase-polymerase chain reaction. Cancer Res., 54:62-68, 1994.
46. Therond, P., Gerbaud, P., Dimon, S., Anderson W. B., Evain-Brion, D., and Raynaud, F. Antioxidant enzymes in psoriatic fibroblasts and erythrocytes. J. Invest. Dermatol, 106:1325-1328, 1996.
47. Ponte, P., Ng, S., Engel, J., Gunning, P., and Kedes, L. Evolutionary conservation in the untranslated regions of actin mRNAs: DNA sequence of a human β-actin cDNA. Nucleic Acids Res., 12:1687-1896, 1984.
48. Sukenaga, Y., Ishida, K., Takeda, T., and Takagi, K. cDNA sequence coding for human glutathione peroxidase. Nucleic Acids Res., 15:7178, 1987.
49. Seidegard, J., Vorachek, W. R., Pero, R. W., and Pearson, W. R. Hereditary differences in the expression of the human glutathione transferase active on trans-stilbene oxide are due to a gene deletion. Proc. Natl. Acad. Sci. USA, 85:7293-7297, 1988.
50. Vorachek, W, R., Pearson, W. R., and Rule, G. S. Cloning, expression, and characterization of a class-mu glutathione transferase from human muscle, the product of the GST4 locus. Proc. Natl. Acad. Sci USA, 88:4443-4447, 1991.
51. Comstock, K. E., Johnson, K. J., Rifenbery, D., and Henner, W. D. Isolation and analysis of the gene and cDNA for a human mu class glutathione S-transferase, GSTM4. J, Biol. Chem., 268:16958-16965, 1993.
52. Takahashi, Y., Campbell, E. A., Hirata, Y., Takayama, T., and Listowsky, I. A basis for differentiating among the multiple human mu-glutathione S-transferases and molecular cloning of brain GSTM5. J. Biol. Chem., 268: 8893-8898, 1993.
53. Campbell, F., Takahashi, Y., Abramovitz, M., Peretz, M., and Listowsky, I. A distinct human testis and brain muμ-class glutathione S-transferase: Molecular cloning and characterization of a form present even in individuals lacking hepatic type μ isoenzymes. J. Biol. Chem., 265:9188-9193, 1990
54. Pemble, S., Scroeder, K. R., Spencer, S. R., Meyer, D. J., Hallier, E., Bolt, H. M, Ketterer, B., and Taylor, J. B. Human glutathione S-transferase θ(GSTT1): cDNA cloning and the characterization of a genetic polymorphism. Biochem. J., 300:271-276, 1994.
55. DeJong, J. L., Morgenstern, R., Jornvall, H., DePierre, J. W., and Tu, D. C. Gene expression of rat and human microsomal glutathione S-transferases. J. Biol. Chem., 263:8430-8436, 1988.

A sequence listing in both computer readable format and paper copies was submitted with This application, both of which are herein incorporated by reference.

What is claimed is:

1. A method to measure expression of multiple target genes in a progenitor cell for bronchogenic, carcinoma comprising:
   using reverse transcription-polymerase chain reaction (RT-PCR) to allow simultaneous expression measurement of the multiple target genes,
   wherein said RT-PCR is quantitative competitive PCR and wherein the quantitative competitive RT-PCR is used to measure mRNA levels of GSTPI, GSTM3 and a glutathione peroxidase (GSHPx) in the progenitor cell,
   wherein the levels of the GSTPI, GSTM3 and GSHPx are significantly lower in bronchogenic carcinoma cells than in normal bronchial epithelial cells.

2. The method of claim 1, in which the progenitor cell comprises a bronchial epithelial cell.

3. The method of claim 1, in which sensitivity for detecting normal bronchial epithelial cells as compared to bronchogenic carcinoma cells is about 90%.

4. The method of claim 1, in which specificity for detecting normal bronchial epithelial cells as compared to bronchogenic carcinoma cells is about 76%.

5. The method of claim 1, comprising
   a) coamplifying a housekeeping gene along with the target genes (to control for the amount of cDNA included in the reaction);
   b) including known amounts of cDNA competitive templates (CTs) for both the target genes and the housekeeping gene;
   c) identifying, choosing primers for synthesizing the competitive templates (CTs) and for amplification of native template (NT) and CT sequences;
   d) comparing the levels of the housekeeping gene CTs to the target gene CTs where the ratio of housekeeping gene CT to each of the target gene CTs is the same;
   e) preparing a master mix that contains the components: dNTPs, buffer, water, Taq polymerise, cDNA and aliquot of CT solution containing known concentrations of CTs for the housekeeping gene and the target genes;
   f) specifying each gene to be amplified in each reaction by the primers included in each reaction by aliquoting separately from the master mix;
   g) determining the amount of cDNA loaded for each sample by comparing the density of PCR product band for housekeeping gene NTcDNA to PCR product band for housekeeping gene CTcDNA; and
   h) determining quantitative expression of the target genes.

6. The method of claim 5, in which the quantitative expression of the target genes is determined by: a) calculating a ratio of target gene NT to CT product; and b) dividing the calculated number of target gene NT molecules by the calculated number of housekeeping gene NT molecules to correct for loading differences.

7. The method of claim 5, in which the housekeeping gene comprises β-actin.

8. The method of claim 7, in which the concentration of the competitive templates (CTs) in each PCR reaction is $10^{-14}$ M for β-actin and varied for each of the other genes.

* * * * *